United States Patent [19]

Gloyer et al.

[11] Patent Number: 4,747,830

[45] Date of Patent: May 31, 1988

[54] ANTI-STICK CONTAGION FREE DISPOSABLE HYPODERMIC SAFETY SYRINGE

[76] Inventors: Walter W. Gloyer, 1010 W. Main St., Tomball, Tex. 77375; Frederick G. Bright, 27311 Springwood Dr., Magnolia, Tex. 77355

[21] Appl. No.: 2,510

[22] Filed: Jan. 12, 1987

Related U.S. Application Data

[63] Continuation-in-part of Ser. No. 856,199, Apr. 28, 1986, abandoned.

[51] Int. Cl.⁴ ............................................. A61M 5/32
[52] U.S. Cl. ................................. 604/110; 604/198
[58] Field of Search ............... 604/110, 162, 192–198, 604/220, 222, 263

[56] References Cited

U.S. PATENT DOCUMENTS

| | | | |
|---|---|---|---|
| 2,688,325 | 9/1954 | Lockhart | 604/220 |
| 3,354,882 | 11/1967 | Coanda | 604/222 |
| 4,459,997 | 7/1984 | Sarstedt | 604/110 |
| 4,562,844 | 1/1986 | Carpenter et al. | 604/220 X |
| 4,573,976 | 3/1986 | Sampson et al. | 604/198 |
| 4,650,468 | 3/1987 | Jennings | 604/194 X |
| 4,655,751 | 4/1987 | Harbaugh | 604/198 |
| 4,675,005 | 6/1987 | De Luccia | 604/110 |

*Primary Examiner*—Dalton L. Truluck
*Attorney, Agent, or Firm*—Guy E. Matthews

[57] ABSTRACT

A disposable safe hypodermic syringe. Includes a hollow barrel formed with a support collar at one end to enclose and releaseably latch a needle support member and a hypodermic needle carried by the support member. The barrel is formed at its distal second end to receive an injection piston carried by the plunger member. The plunger head and needle support member cooperate to form a latch for latching the support member to the plunger head, releasing the support member from the support collar, and withdrawing the plunger head, support member, and needle together to a protective position within the barrel. A latch carried by the injection piston and by the second end of the barrel finally latches the injection piston, plunger head, support member, and needle together to a contagion safe position. Two embodiments are disclosed.

20 Claims, 4 Drawing Sheets

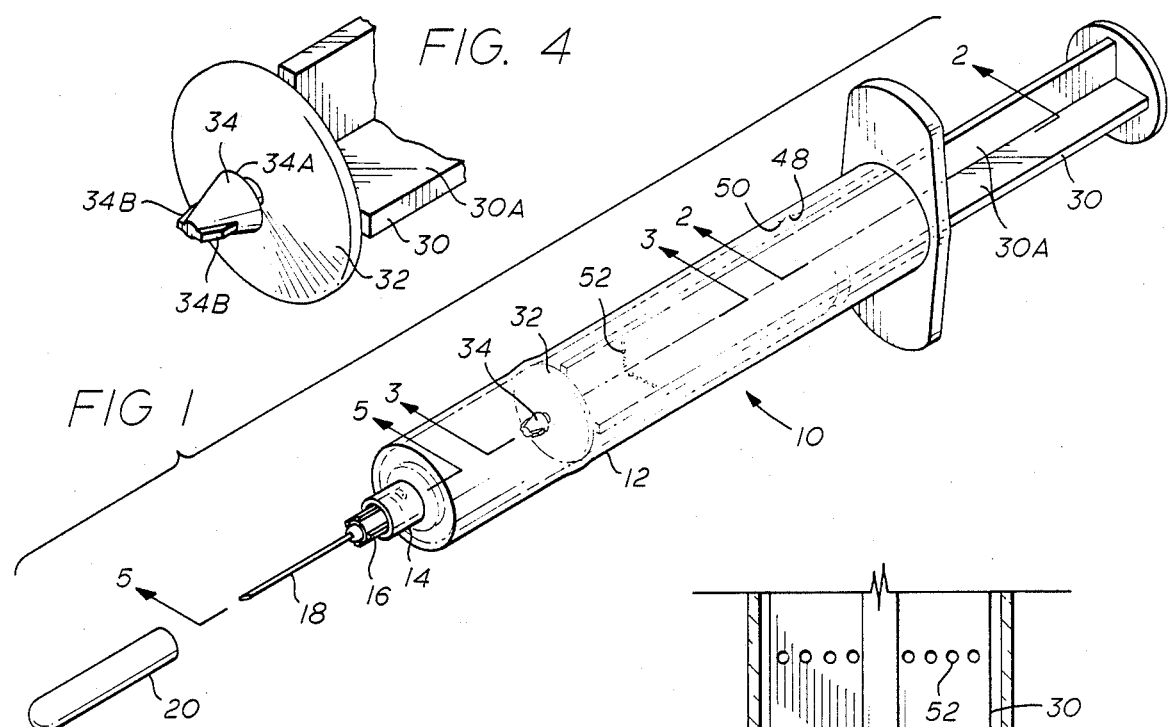
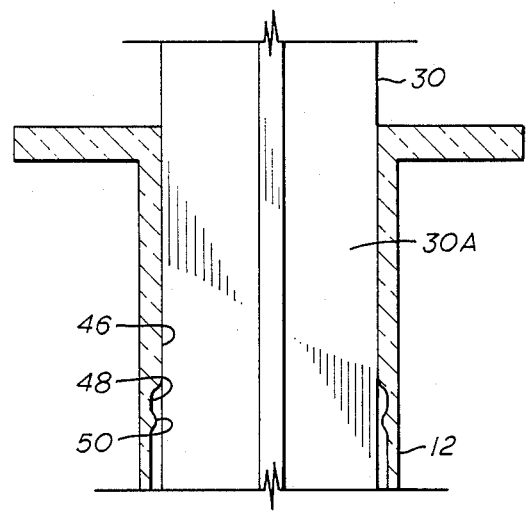
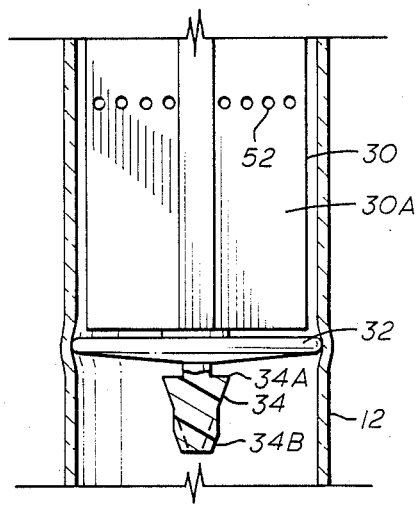
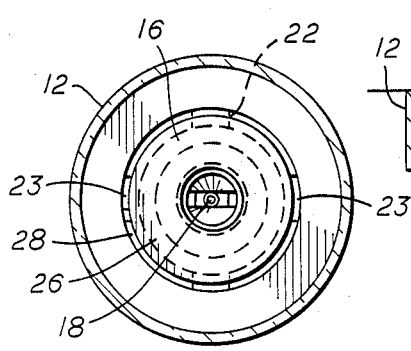
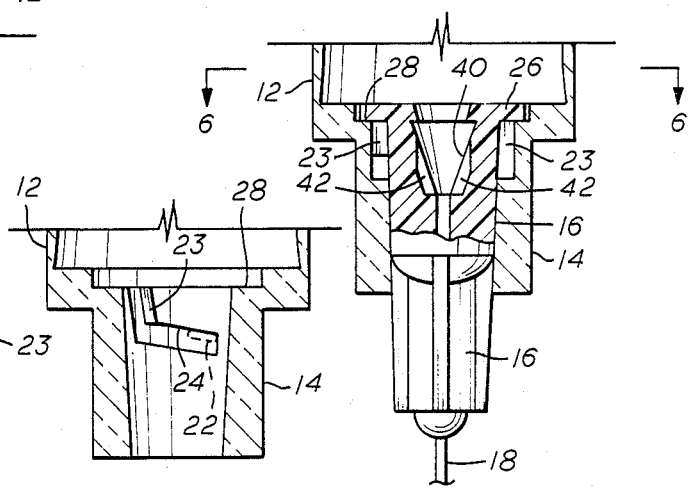

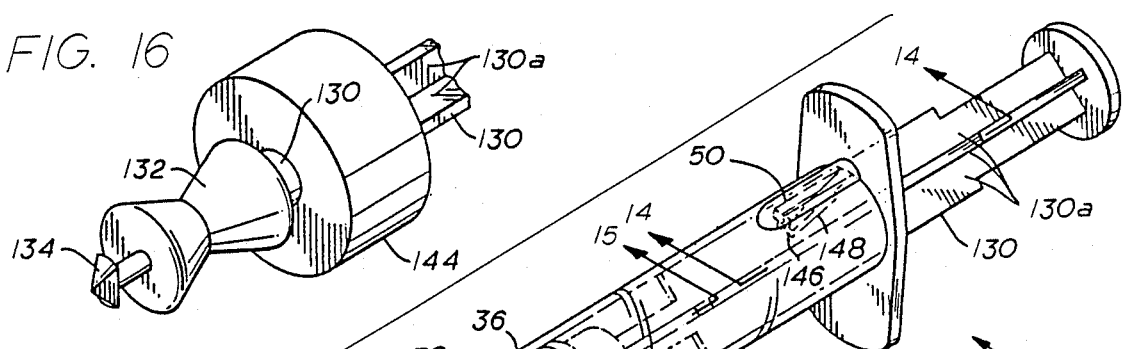
FIG. 16
FIG. 13
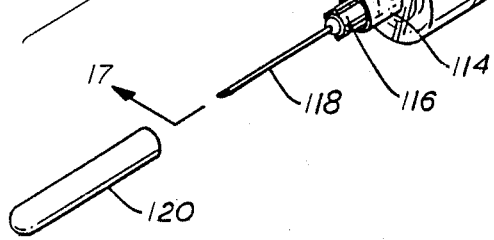
FIG. 14
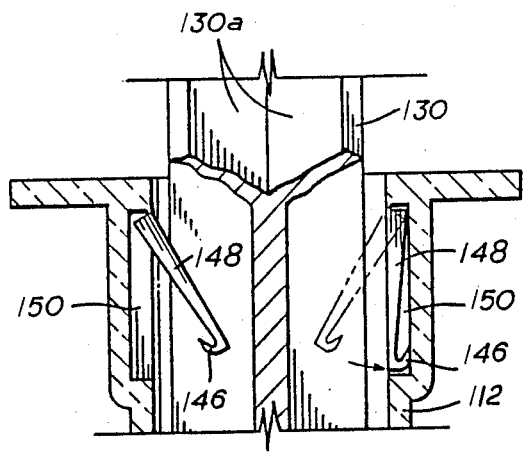
FIG. 15
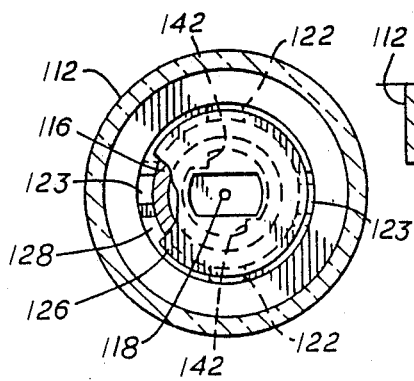
FIG. 18　　FIG. 17A　　FIG. 17

ANTI-STICK CONTAGION FREE DISPOSABLE HYPODERMIC SAFETY SYRINGE

This application is a continuation-in-part of application Ser. No. 856,199 filed Apr. 28, 1986, now abandoned.

FIELD OF THE INVENTION

This invention generally relates to hypodermic syringes of the disposable type and more particularly pertains to a disposable syringe which will positively and effectively shield and guard the syringe needle from sticking or pricking persons handling the syringe after the syringe has been used.

BACKGROUND OF THE INVENTION

In the medical health professions, a health hazard know as "needle stick" exists. The hazard exists because hypodermic syringes do not have the safety features as would prevent a used syringe from accidently sticking (puncturing) the flesh of medical, clean up, and/or other personnel before the syringe is finally disposed of as by incineration or the like.

The needle stick hazard, of course, incurs the possibility of transmitting infectious diseases such as Hepatitis, AIDS, Herpes, and the like through needles which have become contaminated through the course of syringe usage.

The only way that infection from these agents can be positively prevented is by not coming into contact with such agents in the first place. An "anti stick" contagion free disposable hypodermic syringe, as provided by the present invention, creates a barrier by virtue of the syringe structure that will positively prevent such needle stick accidents from occurring.

The presently known prior art is as follows: U.S. Pat. Nos. 1,378,806; 2,400,722; 2,571,653; 3,890,971; 4,356,822; 4,425,120; 2,752,920; 3,937,211; 4,026,287; 4,425,120; 4,507,117. Also noted is that the concept of a cylinder stretched by a piston into sealing relationship during axial movement of the piston within the cylinder, per se, is not considered new.

OBJECT OF THE INVENTION

The principle object of this invention is to provide a contagion safe disposable hypodermic syringe for the prevention of "needle stick" infections.

Another object of the present invention is to provide a contagion safe disposable hypodermic syringe which is reliable, simple to use, and relatively simple and inexpensive to manufacture.

SUMMARY OF THE INVENTION

The foregoing and other objects of the invention are attained in a disposable safe hypodermic syringe which includes a resilient hollow barrel forming a support collar at one end to enclose, releasably latch and support a needle support member and a hypodermic needle carried by the support member. The barrel receives at its second end an injection piston carried by a plunger member. The injection piston is of more rigid construction than the barrel and is of diameter to slightly stretch the barrel in sealed relation during travel of the piston within the barrel. The injection piston and the needle support member cooperate to form a first latch arrangement which (1) latches the support member to the injection piston, (2) releases the support member from the collar, and (3) withdraws the injection piston, the support member, and the needle together as a connected unit to a selected protective position within the barrel. A second latch arrangement including the injection piston and a resilient buttress configuration formed by the barrel near the second end of the barrel serves to finally latch the injection piston, the support member, and the needle together as a unit into the protective position within the barrel. The resilient buttress configuration includes a resilient buttress and circular rib and groove formed within the resilient barrel with the rib being of smaller internal diameter of the barrel and adapted to temporarily stretch in order to permit the injection piston to pass the rib and seat within the groove against further movement.

In another embodiment, the hypodermic syringe includes a hollow barrel formed with a support collar at one end to releasably latch and support a support member and a hypodermic needle carried by the support member. The barrel is formed at its second end to receive a resilient injection piston carried by a plunger head of a plunger member. The plunger head and the needle support member cooperates to form a latch which latches the support member to the plunger head, releases the support member from the support collar and permits withdrawal of the plunger head, the support member, and the needle together to a protective position within the barrel. A hook latching arrangement latches the piston in the protective position.

BRIEF DESCRIPTION OF THE DRAWING

FIG. 1 is a perspective, partially ghosted view of a hypodermic syringe of the present invention;

FIG. 2 is an elevational, partly sectional view of an upper retaining latch of the present invention as taken along the line 2—2 of FIG. 1;

FIG. 3 is an elevational, partly sectional view of the injection piston of the present invention as taken along the lines 3—3 of FIG. 1;

FIG. 4 is a perspective view of the injection piston as shown in FIG. 3;

FIG. 5 is an elevational, partly sectional view of the needle support collar and needle support member as taken along the lines 5—5 of FIG. 1;

FIG. 5A is a view of the needle's support collar as shown in FIG. 5 with the needle support member removed to expose a buttress restraining structure;

FIG. 6 is a partially sectional view taken along the line 6—6 of FIG. 5;

FIG. 13 is a perspective partially ghosted view of an alternate hypodermic syringe of the present invention;

FIG. 14 is a sectional elevational view of an upper retaining latch of the alternate embodiment as taken along the line 14—14 of FIG. 13;

FIG. 15 is a sectional elevational view of the plunger head and displacement piston of the present invention as taken along the lines 15—15 of FIG. 13;

FIG. 16 is a perspective view of the plunger head shown in elevation in FIG. 15;

FIG. 17 is a partially sectional, elevational view of the needle support collar and the needle support member as taken along the line 17—17 of FIG. 13;

FIG. 17A is a view of the needle support collar as shown in FIG. 17 with a needle support member removed to expose a buttress restraining structure;

FIG. 18 is a partially sectional view taken along the line 18—18 of FIG. 17;

DESCRIPTION OF THE PREFERRED EMBODIMENT

Figure 7:
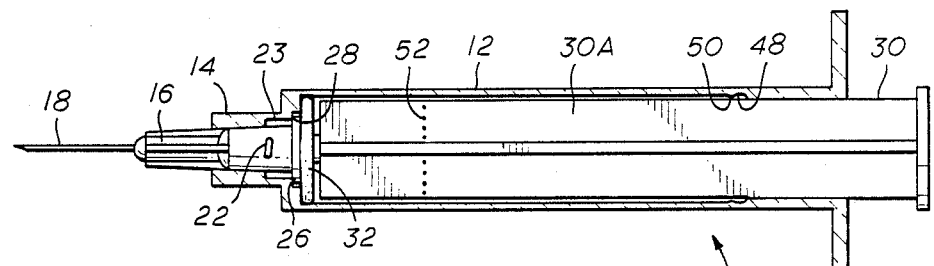
FIG. 7 is a longitudinal partly sectional view of the syringe with the injection piston moved into direct contact with the needle support member to cause the latching engagement of the needle support member as subsequently illustrated in FIGS. 8-10.

Referring now to FIG. 1, the syringe 10 of the present invention is shown in perspective. As seen, the syringe 10 includes a resilient syringe barrel 12 which has formed, on its distal end, a needle support collar 14. Mounted within support collar 14 is a needle support member 16 mounting a hypodermic needle 18. A slip-on sheath 20 is provided to cover the needle 18 and support member 16 until such time as the syringe 10 is to be used.

Referring to FIGS. 5 and 5A, the needle support member 16 is mounted within the mounting collar 14 from within the barrel 12. As shown, the mounting member 16 has formed thereon a pair bayonet lugs 22 which are passed down slots 23 and rotated 90° across an inclined buttress of a thread 24 to be centered in latched position as shown in FIG. 5. Support member 16 has a somewhat resilient flange 26 formed on its upper end which engages and seals against a recessed counter bore 28 as the pin 22 is passed across the buttress of thread 24 into the latched position. Such installation and latching occurs within the barrel 12 as the needle is being assembled before subsequent use as shown in FIG. 1.

Inserted and carried within the barrel 12 is a plunger member 30 comprising a plurality of longitudinal ribs 30A and carrying at its distal end within the barrel 12 a injection piston 32 and a plunger stinger latch 34 as best shown in FIGS. 3-5, and 8. The injection piston 32 may be comprised of a relatively hard material such as Nylon ® for example. Plunger 30 may be provided of a more inelastic material, an acrylic or polystyrene for example, joined to piston 32 as by ultrasonic welding. The outer periphery of injection piston 32 is smooth and rounded to provide sealing engagement to the interior wall of the barrel 12. The barrel 12 may be provided of a resilient material such as polyethelyne or polypropylene, for example. All the materials are to be of "food" grade quality or better.

The piston 32 is of slightly larger diameter than the interior internal diameter of cylinder barrel 12 whereby the barrel 12 is slightly stretched by the injection piston 32 in sealing relationship as the piston 32 is traversed from the inner to the distal end of the barrel 12. Injection piston 32 is of shape and size to serve as a liquid displacement piston within the barrel 12 for the purpose of withdrawing a liquid substance from another vial or vessel, for example, and subsequently injecting the substance through the hypodermic needle 18 into a subject being treated.

Figure 8:
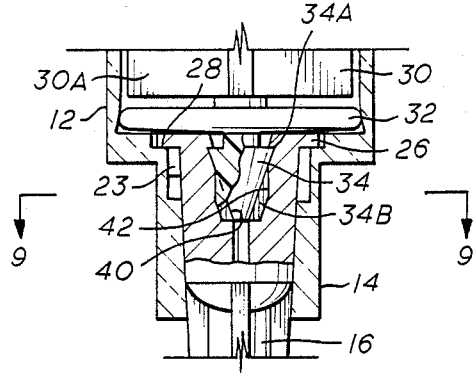
FIG. 8 is a partly sectional view of the injection piston and needle support member as disposed in FIG. 7.

As shown in FIGS. 3, 5, and 8, the injection piston 32 carries a plunger latch stinger 34 which is of conical shape forming a retaining lip 34A around the upper periphery and forming rotational lugs 34B axially along its conical face. As shown in FIGS. 5 and 8-10 the stinger latch 34 is pushed to stretch an inner shoulder of the resilient flange 26 and descend into a recess formed in a support member 16 and into engageable position with a tapered latch seat 40 having complimentary grooves 42 to receive the lugs 34B.

Figure 9:
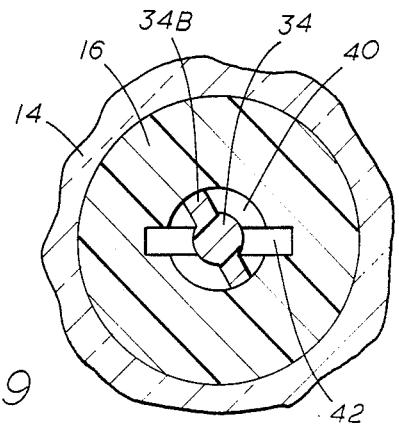
FIG. 9 is a partly sectional view taken at line 9—9 of FIG. 8 and showing the latch stinger inserted into the needle support collar cavity prior to rotating the stinger lugs into registry to complementary latch grooves.
Figure 10:
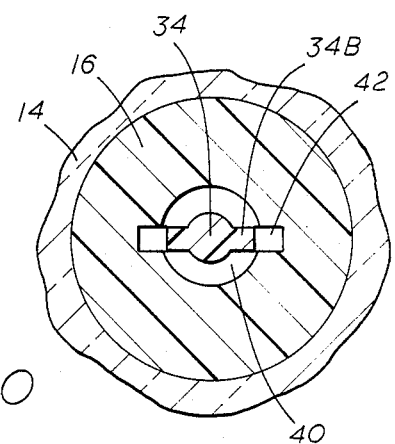
FIG. 10 is the same as FIG. 9 after the stinger lugs have been rotated into registry with the complementary grooves.

When pushed as described, the latch 34 may be rotated slightly at random as shown in FIGS. 9 and 10 to bring lugs 34B into engagement with the grooves 42 and seat 40 where, further rotation of plunger 30, will rotate an assembly including injection piston 32, the support member 16 and the needle 18.

With further reference to FIGS. 5, 5A, and 6, further rotation of the plunger 30 and injection piston 32 through 90° also rotates the support member 16 and its lugs 22 along the support buttress of the thread 24 until the lugs are in alignment with slots 23, whereupon withdrawal of the plunger head 32 back into the barrel 12 also withdraws the needle support member 16 and needle 18 as a unit back into the barrel 12 into complete isolation away from anything that might be scratched or pricked by the needle 18.

Provided in the inner or upper end of the barrel 12 is a land 46 of internal diameter less than the internal diameter of the barrel and forming a buttress. A latching groove 48 is formed, which may be of about the same internal diameter as the internal diameter of the barrel 12, by a latching rib 50. Latching rib 50 is also of internal diameter smaller than the internal diameter of the barrel 12. It is to be noted that the portion of the barrel comprising the land 46 and the latching rib 50 are also of the resilient material provided for the barrel 12 and will also stretch in diameter though, of course, with considerably greater force being required to do such stretching.

As the injection piston 34 is pulled against the rib 50 with somewhat greater force than used to withdraw the piston through the barrel, the rib 50 will also stretch and permit the injection piston 34 to enter into and seat in the groove 48. Once seated within the groove 48, the piston 34 is substantially resistant to movement in either direction.

Figure 11:
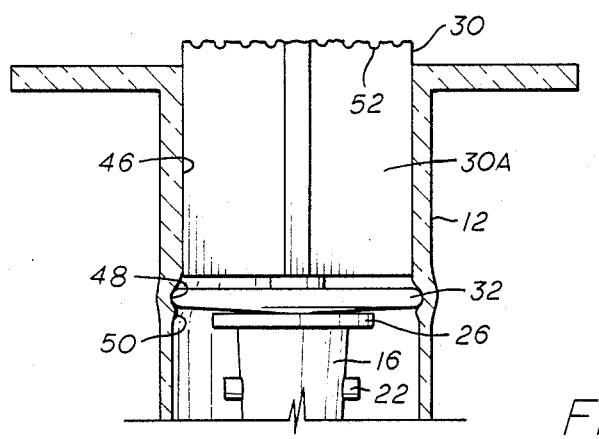
FIG. 11 is an elevational, partly sectional view of the piston and plunger withdrawn into locked and protective position within the barrel as provided.
Figure 12:
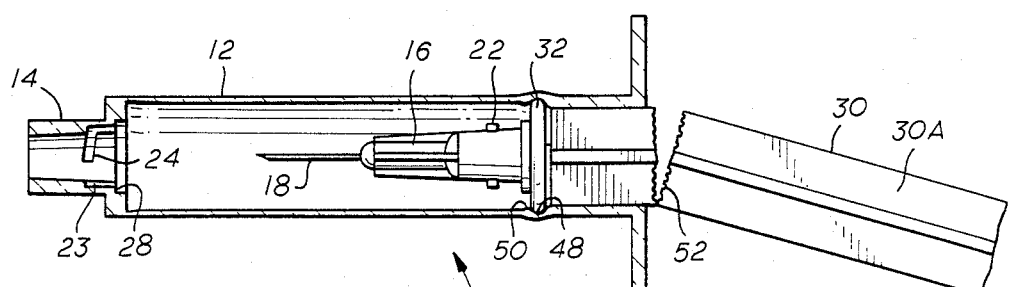
FIG. 12 is an elevational, partly sectional view of the hypodermic syringe with the hypodermic needle in safe looked position and with a portion of the plunger being broken off preparatory to further handling.

The plunger 30 is formed with perforations 52 in the ribs 30A at a location such as to be substantially flush with the end of the barrel 12 when the injection piston 34 is seated in the groove 48. At this time lateral force can be applied to the inner end of the plunger 30 to break off the plunger 30 along the perforations 52, leaving the remainder of the plunger 30 substantially flush with the inner end of the barrel 12 (as shown in FIGS. 11 and 12). As an operable though less positive expedient for fixing piston 34 the rib 50 may be omitted and the elastic stretch of barrel 12 against piston 34 with piston 34 abutting the buttress of land 46 can serve to hold the needle assembly in protective position after plunger 30 has been broken off. Provision of rib 50, as described, is preferable.

Operation of the Preferred Embodiment

The syringe 10 is delivered to the person who will use it assembled together as shown in FIG. 1 with needle mounting member 16 locked into position in support collar 14 with flange 26 sealed against counter bore 28. The injection piston 34 is free to be moved by plunger 30 from below the rib 50 shown in FIGS. 2, 7, 11, and 12 to a position just short of where the latch 34 is latched into the flange 26.

The operator may remove the sheath 20 from the needle 18 and inject the needle 18 into a container to withdraw substance into the barrel 12 for subsequent injection. The operator may then insert the needle 16 into a subject and inject the substance into the subject. Alternately, the operator may insert the needle into the subject while the syringe barrel 12 is empty, withdraw blood from the subject and subsequently discharge the blood into some container for testing or the like.

After the syringe 10 has been used, the injection piston 32 and stinger latch 34 is pushed firmly by the plunger 30 until the stinger latch 34 passes through the flange 26 into the recess within the support member 16 (FIG. 8). The plunger is thereon initially rotated sufficiently to engage the lugs 34A into the accommodating slots 42.

As a continuing motion, the plunger 32 then may be rotated 90° further to rotate the lugs 22 across the supporting buttress of thread 24 to a position where the lugs 22 are in alignment with the release slots 23 (FIGS. 5, 5A, and 6).

The plunger head 32 is then pulled inwardly into the barrel 12 until the position is reached where the injection piston 32 abuts the latch rib 50. With somewhat more force, the plunger head 32 is pulled further to cause the piston 32 to stretch the rib 50 and snap into seating position within the groove 48 where the piston 32 is then latched against return from the groove 48 by the buttress rib 50. Lateral force may then be applied to the end of plunger 30 to break the plunger 30 at the serrations 52, leaving the remainder of the plunger substantially flush with the end of the barrel 12 (FIGS. 11 and 12).

The piston 32 and the attached needle support member 16 and needle 18 are now in a permanently immobile protective position within the barrel 12 (FIGS. 11 and 12).

The used syringe 10 may then be discarded without further precaution against any hazard of "needle stick."

DESCRIPTION OF AN ALTERNATE EMBODIMENT

Referring now to FIG. 13, the syringe 110 of the present invention is shown in perspective. The syringe 110 includes a syringe barrel 112 which has formed on its distal end a needle support collar 114. Mounted within support collar 114 is a needle support member 116 mounting a hypodermic needle 118. A slip on sheath 120 is provided to cover the needle 118 and support member 116 until such time as the syringe 110 is to be used.

Referring to FIGS. 14–17A, the needle mounting member 116 is mounted within the mounting collar 114 from within the barrel 112. As shown, the mounting member 116 has formed thereon a pair of bayonet lugs 122 which are passed down slots 123 and rotated 90° across a buttress of a thread 124 to be centered in latched position as shown in FIG. 117. Mounting member 116 has a somewhat resilient flange 126 formed on its upper end which engages and seals against a recessed counter bore 128 as the pin 122 is passed across the buttress of thread 124 into the latched position. Such installation and latching occurs within the barrel 112 as the needle is being assembled before subsequent use as shown in FIG. 13.

Figure 20:
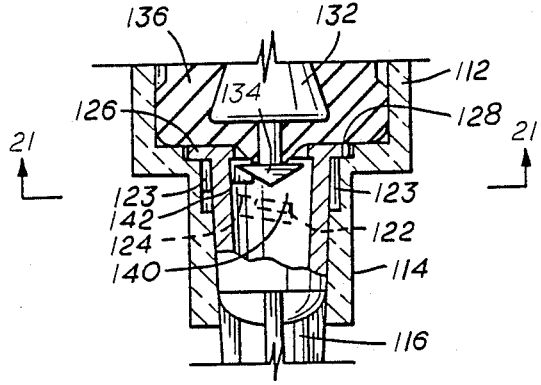
FIG. 20 is a partly sectional detailed view of the displacement piston and needle support member as shown in FIG. 19.

Inserted and carried within the barrel 112 is a plunger member 130 comprising a plurality of longitudinal ribs 130A and carrying at its distal end within the barrel 112 an inwardly facing latch flange 144, a plunger head 132, and a plunger latch 134 as best shown in FIGS. 15 and 20.

The plunger 132 carries a soft resilient injection piston 136 comprised of soft rubber, butyl, latex or the like, which is of shape and size to serve as a liquid displacement piston within the barrel 112 for the purpose of withdrawing a liquid substance from another vial or vessel, for example, and subsequently injecting the substance through the hypodermic needle 118 into a subject being treated.

The forward end of piston 136 is formed as a thin diaphragm 138 which covers the plunger latch 134 in sealed relation during the time that the hypodermic syringe is being used to receive an injectable substance and to inject the substance as previously noted.

Figure 21:
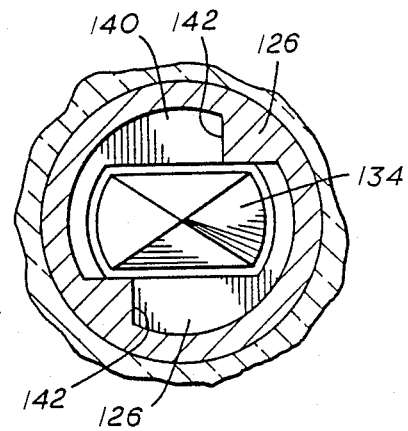
FIG. 21 is a partially sectional view taken at line 21—21 of FIG. 20 and showing the latch protruding from the plunger head by stretching or possibly perforating a diaphragm of the displacement piston preparatory to engagement of the latch within accommodating shoulders of the needle support member.
Figure 22:
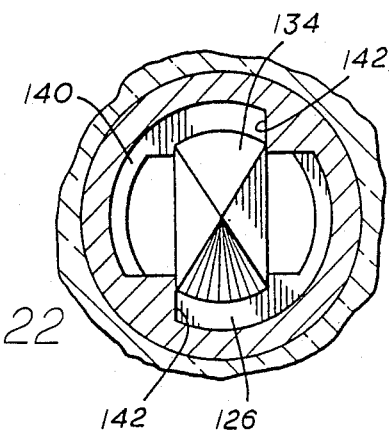
FIG. 22 is the same view as FIG. 21 showing the plunger latch rotated 90° to latch the plunger head into the needle support member.

As shown in FIG. 18 and subsequently in FIGS. 20–22, the plunger latch 134 is pushed to stretch and distend the diaphragm 138 into a recess formed in support member 116 and into engageable position with a plunger latch seat 140. The diaphragm may be ruptured at times.

When pushed out, as shown in FIG. 20, the latch 134 carried by the plunger head 132 may be rotated 90° (as shown between FIGS. 21 and 22) into engagement with a latch stop 142, whereupon the support member 116 and the needle 118 is fixedly attached to the plunger head 132.

With further reference to FIG. 17, 18, 20, and 22, further rotation of the plunger head 132 through 90° also rotates the support member 116 and its lugs 122 along the support buttress of the thread 124 until the lugs are in alignment with the slots 123, whereupon withdrawal of the plunger head 132 back up into the barrel 112 also withdraws the needle support member 116 and needle 118 (as a unit) back into the barrel 112 in complete isolation from anything that might be scratched or pricked by the needle 118. As the plunger 130 is pulled away from the distal end of the barrel 130, the plunger head 132 and the piston 136 are also pulled along as a connected unit.

Figure 24:
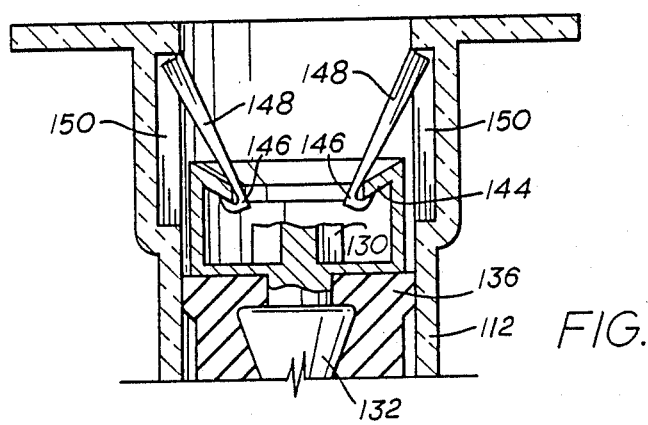
FIG. 24 is an enlarged partly sectional detail of the upper portion of the displacement piston and the upper portion of the barrel as illustrated in FIG. 23 where the upper barrel latches have engaged the latching flange provided on the upper portion of the displacement piston.

It is to be noted in FIGS. 15 and 24 that the piston 136 is mounted at its upper end against the inwardly facing latch flange 144.

Provided in the upper end of the barrel 112 are recessed pockets 150 which accommodate at least two latch hooks 146 carried on latch arms 148 (FIG. 24). The piston 136 is inserted into the barrel as the syringe is assembled. The latch arms 148 carry the latch hooks 146 out into a position where the latch flange 144 will flex the arms 148 in moving past hooks 146, then engage the hooks 146 to prevent movement of the piston 136 back toward the support collar 114.

Thus, when piston 136 is retracted, and when the plunger head 132 has carried the needle support member 114 and the needle 116 back into the protection of the barrel 112, then the hooks 146 are latched on to the retainer flange 144. Thereafter, the needle mount 116 and plunger head 132 are prevented from return movement.

OPERATION OF THE ALTERNATE EMBODIMENT

The syringe 110 is delivered for use assembled together as shown in FIG. 13 with needle mounting member 116 locked into position in support collar 114 with flange 126 sealed against the counter bore 128. The piston 136 is free to be moved by plunger 130 from below the pockets 150, shown in FIGS. 14 and 24, to a position before the diaphragm 138 is stretched or punctured. The operator may remove the sheath 120 from the needle 118 and inject the needle 118 into a container to withdraw substance into the barrel 112 for subsequent injection. The operator may then insert the needle 116 into a subject and inject the substance into the subject.

Alternately, the operator may insert the needle into the subject while the syringe barrel 112 is empty and withdraw blood for testing or the like.

After the syringe 110 has been used, the plunger head 132 and piston 136 is pushed firmly by the plunger 130 into contact with a support member 114 sufficiently to stretch or rupture the diaphragm 138 and bring the plunger latch 134 into the recess within support member 116 (FIG. 20). The plunger is thereon rotated 90° to engage the latch 134 against the latch seat 140 and against the latch stop 142 affixing the support member 114 with the plunger head 132 (FIGS. 21 and 22).

As a continuing motion, the plunger 132 may be rotated another 90° after the support member 116 has been affixed to the plunger head 132 to rotate the lugs 122 across the supporting buttress of thread 124 to a position where the lugs 122 are in alignment with the release slots 123 (FIGS. 17, 17A, and 18).

Figure 19:
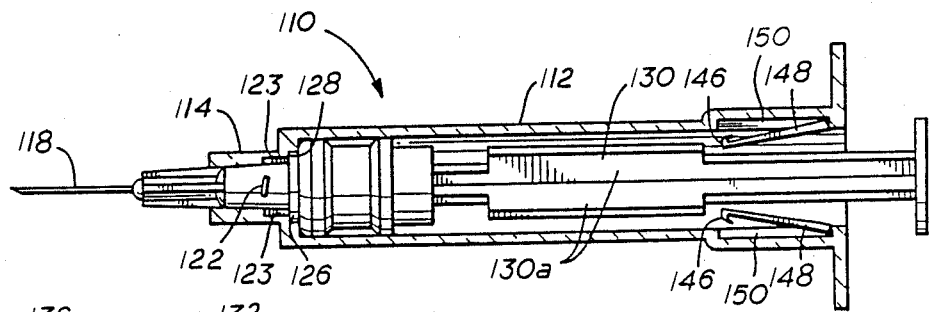
FIG. 19 is a longitudinal, partly sectional view of the syringe with a displacement piston and plunger head moved into direct contact with a needle support member to permit the latching and engagement of the needle support member as subsequently illustrated in FIGS. 20-22.
Figure 23:
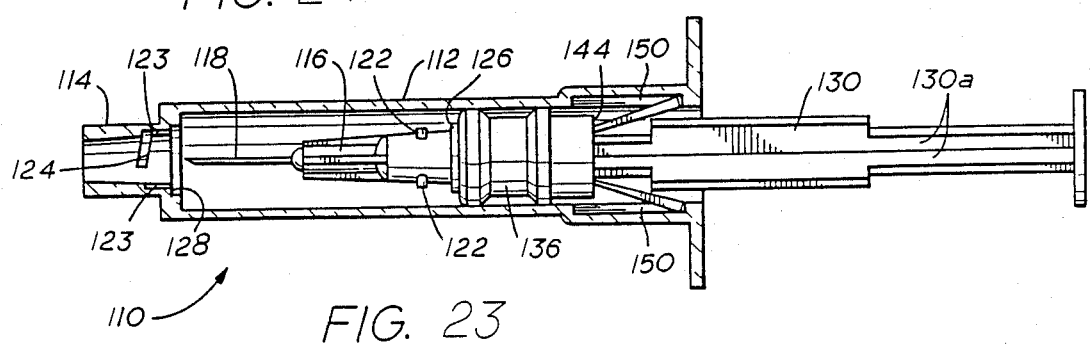
FIG. 23 is the same view as FIG. 19 after the plunger and plunger head has been rotated a first 90° to engage the plunger latch into the needle support (FIGS. 21 and 22) and then a second 90° to disengage the needle support member from the latch buttress located within the support collar of the barrel (FIG. 17, 17A, and 18)

The plunger head 132 is then pulled inwardly into the barrel 112 until the position is reached where the latch flange 144 on the injection piston 136 has become latched with the hooks 146 to engage the latch arms 148 with the upper end or inner end of the barrel 112 (FIGS. 19 and 23).

The plunger 130 and the attached needle support member 116 and needle 118 are now in a permanently immobile position within the barrel 112 (FIG. 23).

The used syringe 110 may then be discarded without further precaution against any hazard or "needle stick." As with Fig. 12, perforations may be provided to break off the extending end of plunger 130 if desired.

It is to be understood that various changes and modifications may be made to the structure of the embodiments as herein disclosed with such modification and changes all coming within the spirit of the invention and the scope and the purview of the appended claims.

What is claimed is:

1. A disposable safe hypodermic syringe comprising in combination:
   (a) a resilient hollow barrel formed with a support collar at one end to enclose and releasably latch a flanged needle support member, said support collar provided with an interior counter bore for seating said flanged needle support member;
   (b) said needle support member carrying a hypodermic needle within said support collar, said needle support member and said hypodermic needle forming a single piece;
   (c) an injection piston received into the second end of said barrel and carried by a plunger member with said injection piston being more rigid than said barrel and being of diameter to slightly stretch said barrel in sealed relation throughout the length of travel of said injection piston within said barrel;
   (d) said injection piston and said needle support member having means cooperating to form first latch means for: (1) latching said support member to said injection piston; (2) releasing said support member from within said collar; and (3) withdrawing said injection piston, said support member and said needle together as a connected unit to a sealed protective position within said barrel; and
   (e) a latch means comprising said injection piston and resilient buttress means formed within said barrel near said second end of said barrel to restrain said injection piston, said support member and said needle together as a unit into said protective position within said barrel.

2. The syringe of claim 1 wherein said resilient buttress means comprises a resilient circular rib and a resilient buttress forming a groove within said resilient barrel with said rib being of smaller internal diameter than the internal diameter of said barrel and adapted to be temporarily stretched by said injection piston to permit said injection piston to pass said rib and to seat within said groove.

3. The syringe of claim 1 further including needle support latch means for latching then releasing said needle support means from within said support collar.

4. The syringe of claim 3 wherein said needle support latch means comprises latching lug means constrained against lug buttress means.

5. The syringe of claim 2 wherein said first latch means comprises a plunger latch means carried by said injection piston an adapted to be rotated and latched within a plunger latch seat means carried within needle support member whereby further rotation of said injection piston will release said needle support member from said support collar and permit said injection piston and said support member to be withdrawn to within said barrel as a unit.

6. The syringe of claim 1 wherein said plunger member is formed with a frangible section adapted to be readily separated at the second end of said barrel when said injection piston is disposed in said protective position.

7. The syringe of claim 1 wherein said injection piston is formed of a relatively rigid plastic and said barrel is formed of a material more resilient than said injection piston.

8. The syringe of claim 1 wherein said injection piston is formed of Nylon and said barrel is formed of a material more resilient than Nylon.

9. The syringe of claim 1 wherein said barrel is formed of a material from the group consisting essentially of polyethlyene and polypropylene.

10. The syringe of claim 2 further including needle support latch means for latching then releasing said needle support means from within said support collar and wherein said needle support latch means comprises lathing lug means constrained against lug buttress means.

11. The syringe of claim 10 wherein said plunger member is formed with a frangible section adapted to be readily separated at the second end of said barrel when said injection piston is disposed in said protective position.

12. A disposable safe hypodermic syringe comprising in combination:
(a) a resilient hollow barrel formed with a support collar at one end to enclose and releasably latch a flanged needle support member, said support collar provided with an interior counter bore for sealing said needle support member;
(b) said needle support member carrying a hypodermic needle within said support collar, said needle support member and said hypodermic needle forming a single piece;
(c) an injection piston received into the second end of said barrel and carried by a plunger member with said injection piston being more rigid than said barrel and being of diameter to slightly stretch said barrel in sealed relation throughout the length of travel of said injection piston within said barrel;
(d) said injection piston having stinger means and said needle support member having means cooperating with said stinger means to form first latch means for:
(1) latching said support member to said injection piston;
(2) releasing said support member from within said collar; and
(3) withdrawing said injection piston, said support member and said needle together as a connected unit to a selected protective position within said barrel; and
(e) a second latch means comprising said injection piston and resilient buttress means formed within said barrel near said second end of said barrel to restrain said injection piston, said support member and said needle together as a unit into said protective position within said barrel.

13. The syringe of claim 12 wherein said resilient buttress means comprises a resilient circular rib and a resilient buttress forming a groove within said resilient barrel with said rib being of smaller internal diameter than the internal diameter of said barrel and adapted to be temporarily stretched by said injection piston to permit said injection piston to pass said rib and seat within said groove.

14. A disposable safe hypodermic syringe comprising in combination:
(a) a hollow barrel formed with a support collar at one end to releasably latch and support a flanged needle support member, said support collar provided with an interior counter bore for sealing said support member;
(b) said flange needle support member carrying a hypodermic needle within said support collar, said needle support member an said hypodermic needle forming a single piece;
(c) a resilient injection piston received within said barrel from its second end and carried by a plunger head of a plunger member;
(d) said plunger head and said needle support member having means cooperating to form a first latch means for latching said support member to said plunger head, releasing said support member from within said collar, and withdrawing said plunger head, said support member and said needle together as an integral unit to a selected position within the barrel; and
(e) a second latch means carried by said injection piston and by said second end of the barrel to finally latch said injection piston, said plunger head, said support member and said needle together as integral unit into said protective position within said barrel.

15. The syringe of claim 14 wherein said syringe is previously assembled with said needle support member assembled and latched for subsequent release from within said support collar by said plunger head.

16. The syringe of claim 14 wherein said syringe is previously assembled with said member assembled and latched for subsequent release from within said support collar by said plunger head and wherein said first latch means comprises latching lug means constrained against buttress means receiving said lug means.

17. The syringe of claim 14 wherein said syringe is previously assembled with said member assembled and latched for subsequent release from within said support collar by said plunger head and wherein said first latch means comprises a plunger latch means carried by said plunger head adapted to be rotated and latched within a plunger latch seat means carried within said support member whereby further rotation by said plunger head will release said support member from said support collar and permit said plunger head and such support member to be withdrawn within said barrel as an integral unit.

18. The syringe of claim 14 wherein said syringe is previously assembled with said member assembled and latched for subsequent release from within said support collar by said plunger head and wherein said first latch means comprises a plunger latch means carried by said plunger head adapted to be rotated and latched within a plunger latch seat means carried within said support member whereby further rotation by said plunger head will release said support member from said support collar and permit said plunger head and such support member to be withdrawn within said barrel as an integral unit; and wherein said second latch means comprises latch hook means mounted at said second end of said hollow barrel which engage latch flange means carried with said plunger head whereby to latch said plunger head, said needle support member and said needle as an integral unit within said barrel.

19. The combination of claim 14 wherein said first latch means comprises a plunger latch means carried by said plunger head adapted to be rotated and latched within a plunger latch seat means carried within said support member whereby further rotation by said plunger head will release said support member from said support collar and permit said plunger head and said support member to be withdrawn within said barrel as a connected unit.

20. The syringe of claim 19 wherein said second latch means comprises latch hook means mounted at the end of said hollow barrel which engage latch flange means carried with said plunger head whereby to latch said plunger head and said needle support member and said needle as connected within said barrel.

* * * * *